United States Patent
Balkenhohl et al.

(10) Patent No.: US 6,214,608 B1
(45) Date of Patent: *Apr. 10, 2001

(54) RESOLUTION OF RACEMATES OF PRIMARY AND SECONDARY HETEROATOM-SUBSTITUED AMINES BY ENZYME-CATALYZED ACYLATION

(75) Inventors: Friedhelm Balkenhohl, Limburgerhof; Klaus Ditrich, Gönnheim; Christoph Nübling, Hassloch, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/875,417

(22) PCT Filed: Jan. 20, 1996

(86) PCT No.: PCT/EP96/00234

§ 371 Date: Jul. 28, 1997

§ 102(e) Date: Jul. 28, 1997

(87) PCT Pub. No.: WO96/23894

PCT Pub. Date: Aug. 8, 1996

(30) Foreign Application Priority Data

Feb. 3, 1995 (DE) .............................. 195 03 605
Jun. 29, 1995 (DE) .............................. 195 23 151

(51) Int. Cl.$^7$ .................................................. C12P 41/00
(52) U.S. Cl. ............................................................ 435/280
(58) Field of Search ............................................. 435/280

(56) References Cited

U.S. PATENT DOCUMENTS

| | | | |
|---|---|---|---|
| 5,057,607 | 10/1991 | Zmijewski et al. ................. | 540/364 |
| 5,512,454 | * 4/1996 | Usher et al. ........................... | 435/47 |
| 5,728,876 | 3/1998 | Balkenhohl et al. ................ | 564/136 |

FOREIGN PATENT DOCUMENTS

222561 * 5/1987 (EP).
95/08636 * 3/1995 (WO).

OTHER PUBLICATIONS

Zamost et al., "Thermostable Enzymes for Industrial Applications", J. Ind. Microbiol. 8 (2) :71–81 (1991).*
O'Hagan et al., "Steroelectronic influence of fluorine in enzyme resolutions of alpha fluroresters", J. Chem. Soc., Perkin Trans. 2 (1) : 3–4 (1994).*
Fernandez et al., "Lipase–catalyzed enantioselective acylation of N–protected or unprotected 2–aminoalkan–1–ols", J. Chem. Soc., Perkin Trans. 1 (21) : 2885–9 (1992).*
Francalanci et al., "Lipase–catalyzed resolution of chiral 2–amino 1–alcohols", J. Org. Chem. 52 (23) : 5079–82 (1987).*
Iida et al., "Synthesis of optically pure carbon–13 labelled propionate from alanine . . .", J. Labelled Compd. Radiopharm. 29 (2) : 201–216 (1991).*
Sonnet et al., "Kinetic resolution of secondary alcohols with commercial lipases: application to rootworm sex peromone synthesis", J. Chem. Exol. 13 (5) : 1279–92 (1987).*
Gardossi et al., "Selective Acylation of Peptides Catalyzed by Lipases in Organci Solvents", J. Am. Chem. Soc. 113 : 6328–29 (1991).*
J. Chem. Soc., Perkin Trans. 1 (1993), Gotor et al., 2453–6.

* cited by examiner

Primary Examiner—Sandra E. Saucier
(74) Attorney, Agent, or Firm—Keil & Weinkauf

(57) ABSTRACT

A process for preparing optically active primary and secondary heteroatom-substituted amines from the corresponding racemates, which comprises a) enantioselective acylation of a racemic heteroatom-substituted amine with an ester whose acid component carries a fluorine, nitrogen, phosphorus, oxygen or sulfur atom in the vicinity of the carbonyl carbon, in the presence of a hydrolase, b) separation of the mixture of optically active heteroatom-substituted amine and optically active acylated heteroatom-substituted amine to obtain one enantiomer of the heteroatom-substituted amine, c) if required isolation of the other enantiomer of the heteroatom-substituted amine from the acylated heteroatom-substituted amine by amide cleavage.

15 Claims, No Drawings

RESOLUTION OF RACEMATES OF PRIMARY AND SECONDARY HETEROATOM-SUBSTITUED AMINES BY ENZYME-CATALYZED ACYLATION

The present invention relates to a novel process for resolving racemates of primary and secondary heteroatom-substituted amines by reaction with an ester in the presence of a hydrolase and subsequent separation of the enantioselectively acylated heteroatom-substituted amine from the other, unreacted, enantiomer of the heteroatom-substituted amine.

WO 95/08636 describes a process for resolving racemates of primary and secondary amines by reaction with an ester in the presence of a hydrolase. The preferred amines mentioned therein are primary arylalkylamines. However, there is no reference to the usability of heteroatom-substituted amines.

We have now found, surprisingly, that the process described at the outset functions particularly advantageously when the heteroatom-substituted amine used is an amine of the general formula I

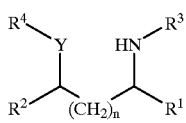

I where n is 0, 1, 2, 3;

Y is O, S, NH, $NR^5$;

$R^1$, $R^2$ are each, independently of one another, H, alkyl, or aryl or $R^1$ and $R^2$ or $R^2$ and $R^3$, or $R^1$ and $R^4$ are, together with the adjacent carbon atoms, part of a ring system;

$R^4$ is alkyl or arylalkyl;

$R^3$, $R^5$ are, independently of one another, H, alkyl or arylalkyl.

We have also found a process for preparing acylated primary and secondary amines by reacting the heteroatom-substituted amines with an ester with specific catalysis by a hydrolase, wherein the acid component of the ester carries a fluorine, nitrogen, phosphorus, oxygen or sulfur atom in the vicinity of the carbonyl carbon.

The esters suitable for the process according to the invention are those which carry in the acid component of the ester an electron-rich heteroatom in the vicinity of the carbonyl carbon or in which an acceptor substituent in the form of one or more heteroatonms is located in the vicinity of the carbonyl carbon in the acid component.

The heteroatom must have at least one free pair of electrons. It can be a fluorine, nitrogen, phosphorus, oxygen or sulfur atom.

It should be located in the vicinity of the carbonyl carbon. This means that the heteroatom is bonded to a carbon atom in the position alpha, beta or gamma to the carbonyl carbon. The heteroatom can also be multiply bonded to the carbon as in the cyano group. Preferred acid components in the ester are those in which the heteroatom is bonded to the alpha carbon atom. Oxygen is preferred as heteroatom.

The heteroatom may also be linked to other groups, eg. alkyl groups. If the heteroatom is, for example, oxygen, an ether moiety is present.

Particularly suitable esters are those having the structure

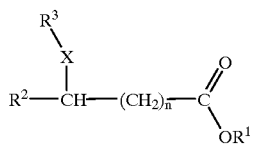

where $R^1 = C_1 - C_{10}$-alkyl, $R^2 = C_1 - C_{10}$-alkyl, H $R^3 =$ H, $C_1 - C_{10}$-alkyl, or phenyl which is unsubstituted or substituted by $NH_2$, OH, $C_{1-4}$-alkoxy or halogen,

X=O, S, $NR^4$, $R^4 =$ H, $C_1 - C_{10}$-alkyl, or phenyl which is unsubstituted or substituted by $NH_2$, OH, $C_{1-4}$-alkoxy or halogen, n=0, 1 or 2.

Of these, the $C_{1-4}$-alkyl esters of $C_{1-4}$-alkoxyacetic acids are preferred, such as ethyl methoxyacetate.

A large number of enzymes can be used as hydrolases in the process according to the invention. Proteases and, in particular, lipases, are preferably used. Particularly suitable lipases are microbial lipases which can be isolated, for example, from yeasts or bacteria. Particularly suitable lipases are those from Pseudomonas, eg. Amano P or the lipase from Pseudomonas spec. DSM 8246.

Further particularly suitable hydrolases are the enzymes commercially obtainable from Novo Nordisk (Enzyme Toolbox), in particular lipases SP 523, SP 524, SP 525, SP 526 and Novozym® 435. These enzymes are microbial lipases which can be prepared from yeasts such as *Candida antarctica*.

It is furthermore possible and advantageous to employ the lipases "Chirazyme L1 bis L8', which are commercially obtainable (Boehringer Mannheim) in the process according to the invention.

The enzyme can be employed in native or immobilized form. The immobilized enzyme Novozym® 435 is particularly suitable.

The processes according to the invention can be carried out in the presence or absence of solvents.

Organic solvents are generally suitable as solvents. The reaction takes place particularly well in ethers, for example in MTBE, 1,4-dioxane or THF, or in hydrocarbons such as hexane, cyclohexane, toluene or halogenated hydrocarbons such as methylene chloride.

The reaction of the ester with the racemic heteroatom-substituted amine with enzyme catalysis is normally carried out at room temperature. The times for this reaction are from 1 to 48 hours, depending on the substrate. Secondary heteroatom-substituted amines usually require longer reaction times than do primary heteroatom-substituted amines. The lower reactivity of secondary heteroatom-substituted amines can also be compensated by increasing the amount of catalyst by comparison with primary heteroatom-substituted amines.

0.5–3 mol of ester are added per mol of amine to be reacted. 0.5–3, preferably 0.5–1.0, mol of ester are added even when racemic substrates are used.

The amount of enzyme to be added depends on the nature of the hydrolase and the activity of the enzyme preparation. The optimal amount of enzyme for the reaction can easily be determined by simple preliminary tests. As a rule, 1000 units of lipase are added per mmol of heteroatom-substituted amine.

The progress of the reaction can easily be followed by conventional methods, for example by gas chromatography. In the case of racemate resolution, it is sensible to terminate the reaction when 50% of the racemic heteroatom-substituted amine is reacted.

This normally takes place by removing the catalyst from the reaction, for example by filtering off the enzyme.

The enantioselective reaction of the racemic substrate with the ester results in the correspondingly acylated product (amide) from one enantiomer, while the other enantiomer remains unchanged. The resulting mixture of heteroatom-substituted amines and amide can easily be separated by conventional methods. For example, extraction or distillation processes are very suitable for separating the mixture of amine and amide.

The process according to the invention is particularly advantageously suitable for acylating heteroatom-substituted amines of the formula I. It can also be used to resolve racemates of virtually all primary and secondary heteroatom-substituted amines. It takes place particularly well with primary amino alcohols, especially those in which $R^4$ is arylalkyl, in particular benzyl, or alkyl, in particular methyl.

Further preferred compounds of the formula I are those where $R^1$ and $R^2$ form with the adjacent carbon atoms a ring system, in particular those of the following structure

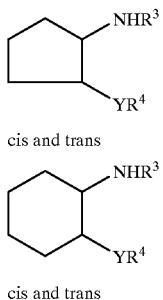

cis and trans or $R^2$ and $R^3$ are part of a ring system, in particular those of the following structure

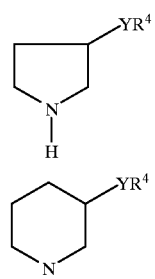

or $R^1$ and $R^4$ are part of a ring system, in particular those of the following structure

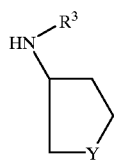

-continued

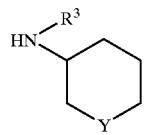

Surprisingly, the reaction of heteroatom-substituted amines of the formula I takes place with very much higher optical yields than the similar reaction of non-heteroatom-substituted amines or those substituted differently from formula I.

Furthermore, as a consequence of the high selectivity and reactivity of the process according to the invention, only a small, or no, excess of acylating agent is needed, which greatly facilitates subsequent separation and purification.

The invention is also suitable for preparing optically active primary and secondary heteroatom-substituted amines from the corresponding racemates, by
 a) enantioselective acylation of a racemic heteroatom-substituted amine with an ester whose acid component carries a fluorine, nitrogen, oxygen or sulfur atom in the vicinity of the carbonyl carbon, in the presence of a hydrolase,
 b) separation of the mixture of optically active heteroatom-substituted amine and optically active acylated heteroatom-substituted amine to obtain one enantiomer of the heteroatom-substituted amine,
 c) if required isolation of the other enantiomer of the heteroatom-substituted amine from the acylated heteroatom-substituted amine by amide cleavage.

The process according to the invention can be made even more economic if, after removal of the required enantiomer, the remaining unwanted enantiomer is racemized and employed anew in the process. This recycling makes it possible to obtain a total of more than 50% of the required enantiomer from the racemic heteroatom-substituted amine.

Not only are the processes according to the invention suitable for producing optically active primary and secondary heteroatom-substituted amines, they can also form part of complicated multi-stage chemical syntheses, for example in the preparation of medicinal agents or crop protection agents.

The following examples illustrate the invention.

EXAMPLE 1

General Method for the Lipase-catalyzed Acylation of Heteroatom-substituted Amines 10 mmol of the primary or secondary heteroatom-substituted amine are dissolved in MTBE (=methyl tert-butyl ether) (about 10% strength solution). 11 mmol of ethyl methoxyacetate are added to the solution and the reaction is started by adding 100 mg of lipase (about 1000 U/mg, Pseudomonas spec. DSM 8246). When the reaction is complete (12–48 h, depending on the heteroatom-substituted amines), the enzyme is filtered off, and the solution is concentrated under reduced pressure. The methoxyacetamides are obtained in a yield of more than 90%.

EXAMPLE 2

General Method for Racemate Resolution

The primary or secondary heteroatom-substituted amine is dissolved in MTBE (about 10% by weight). Addition of 1 mol of ethyl methoxyacetate per mol of racemic heteroatom-substituted amine is followed by that of Pseudomonas lipase (DSM 8246) and the suspension is stirred at room temperature. About 10,000 units of lipase (10 mg) are added per mmol of heteroatom-substituted amine. After 50% reaction has occurred (checked by gas chromatography), which takes 1–48 h depending on the heteroatom-substituted amines, the enzyme is filtered off. The mixture of heteroatom-substituted amines and acylated heteroatom-substituted amine (amide) is separated by distillation or extraction.

EXAMPLE 3

Racemate Resolution with Solvent

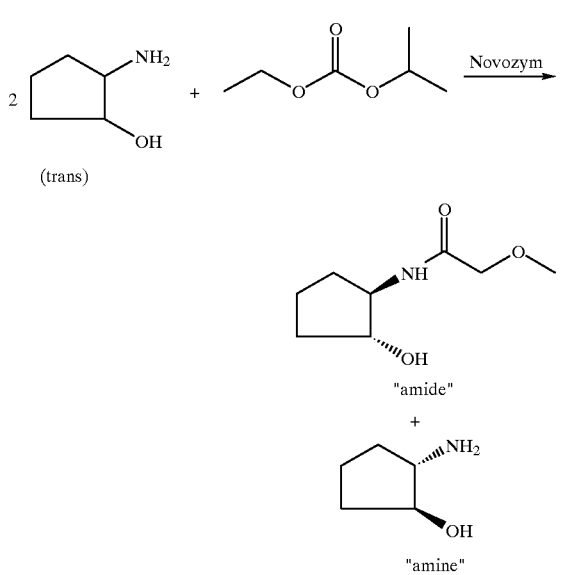

5 g (49.5 mmol) of trans-2-aminocyclopentanol were dissolved in 20 ml of 1,4-dioxane, 3.3 g (25 mmol) of isopropyl methoxyacetate were added and, after addition of 0.1 g of Novozym 435®, shaken at room temperature. After 12 h, $^1$H-NMR showed 50% reaction of amine; the enzyme was filtered off, the filtrate was concentrated, and the unreacted amine was removed from the amide by distillation.

Yields

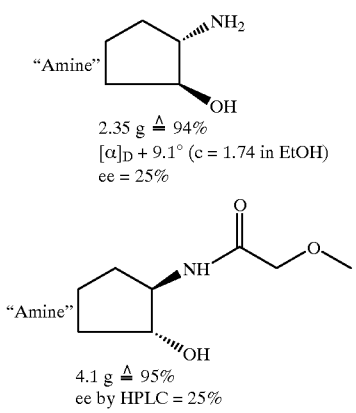

EXAMPLE 4

Racemate Resolution Without Solvent

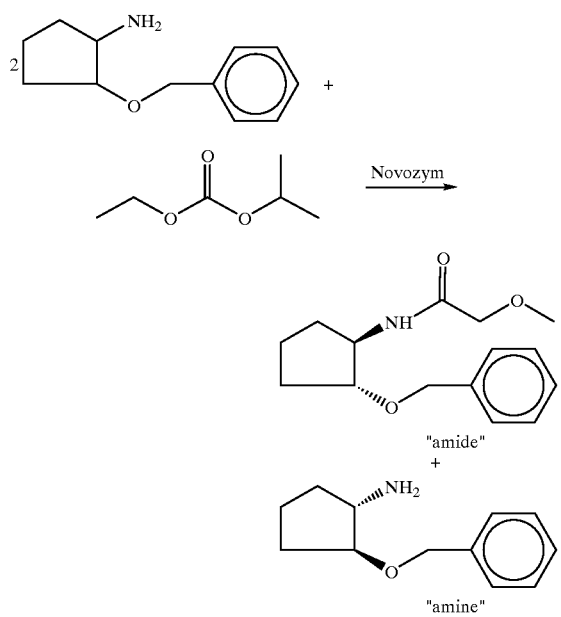

5 g (2 mmol) of trans-2-benzyloxy-1-cyclopentylamine and 1.8 g (13.4 mmol) of isopropyl methoxyacetate were mixed, 0.1 g of Novozym 435® was added, and the mixture was shaken at room temperature. $^1$H-NMR showed 50% reaction of amine after 120 h. The enzyme was filtered off and the 'amine' was separated from the 'amide' by extraction with 10% strength hydrochloric acid.

Yields

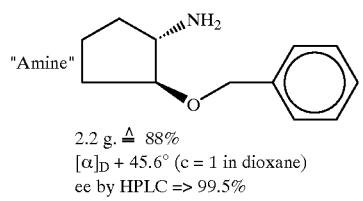

2.2 g. ≙ 88%
[α]$_D$ + 45.6° (c = 1 in dioxane)
ee by HPLC => 99.5%

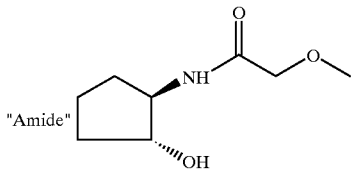

4.9 g. ≙ 92%
[α]$_D$ + 6.0° (c = 1 in dioxane)
ee by HPLC = 93%

EXAMPLE 5

Further Racemate Resolutions

The following reactions (see Table) were carried out as in Example 3 or 4.

TABLE

| Starting material | Preparation as in Example | Conversion [%] | Amine Rotation* | Amine ee | Amide Rotation* | Amide ee |
|---|---|---|---|---|---|---|
| 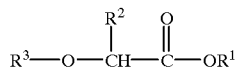 | 3 | 50 | −1.5° (c = 1 in ethanol) | 24% | — | 26% (by HPLC) |
| 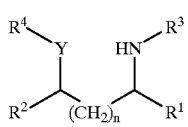 | 3 | 50 | +4.9°(HCl adduct) (c = 1 in CHCl₃) | >95% (by HPLC) | +28° (c = 1 in dioxane) | >99.5% (by HPLC) |
|  | 4 | 50 | +4.8°(HCl adduct) (c = 1 in CHCl₃ +9.8° (c = 1 in dioxane) | >95% (by HPLC) | +27.5° c = 1 in dioxane | >99.5% (by HPLC) |
| 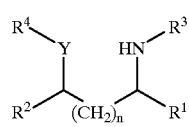 | 4 | 42 |  | 70% | — | 99.5% (by HPLC) |

*The rotations were measured with the Na-D line at room temperature.

The table in Example 5 shows that very much higher optical purities can be obtained on use of 'protected' amino alcohols in which the oxygen atom is, for example, adjacent to a benzyl or methyl group than on use of unprotected amino alcohols.

We claim:

1. A process for preparing acylated primary and secondary oxygen or nitrogen substituted amines by reacting the oxygen or nitrogen substituted amines with an ester of the formula:

$$R^3\text{—O—CH(R^2)—C(=O)—OR}^1$$

where
  $R_1 = C_1\text{–}C_{10}$-alkyl,
  $R^2 = C_1\text{–}C_{10}$-alkyl or H,
  $R^3 = $ H, $C_1\text{–}C_{10}$-alkyl, or phenyl which is unsubstituted or substituted by $NH_2$, OH, $C^{1-4}$-alkoxy or halogen, in the presence of a lipase selected from the group consisting of SP 523, SP 524, SP 525, SP 526 and Novozym® 435.

2. The process of claim 1 wherein the oxygen or nitrogen substituded amine reacted is a compound of the formula I:

$$R^4\text{—Y—CR}^2\text{—(CH}_2\text{)}_n\text{—CHR}^1\text{—NHR}^3$$ (I)

where
  n is 0, 1, 2, 3;
  Y is O, NH, or $NR^5$;
  $R^1$, $R^2$ are each, independently of one another, H, alkyl, or aryl or $R^1$ and $R^2$, or $R^2$ and $R^3$, or $R^1$ and $R^4$ are, together with adjacent carbon atoms, part of a ring system;
  $R^4$ is alkyl or arylalkyl;
  $R^3$, $R^5$ are, independently of one another, H, alkyl or arylalkyl.

3. The process of claim 2 wherein, in the ester, $R^1$ is $C_1\text{–}C_4$-alkyl and $R^2$ is $C_1\text{–}C_4$-alkyl.

4. The process of claim 3 wherein in the ester is ethyl methoxyacetate.

5. A process for resolving racemates of primary and secondary oxygen or nitrogen substituted amines by reacting the oxygen or nitrogen substituted amines with an ester of the formula:

$$R^3\text{—O—CH(R^2)—C(=O)—OR}^1$$

where
  $R^1 = C_1\text{–}C_{10}$-alkyl,
  $R^2 = C_1\text{–}C_{10}$-alkyl or H,
  $R^3 = $ H, $C_1\text{–}C_{10}$-alkyl, or phenyl which is unsubstituted or substituted by $NH_2$, OH, $C_{1-4}$-alkoxy or halogen, in the presence of a lipase selected from the group consisting of SP523, SP524, SP525, SP526 and Novozym® 435 and subsequently separating the oxygen or nitrogen substituted amine, which has undergone enantioselective acylation, from the other unreacted enantiomer of the heteroatom-substituted amine.

6. The process of claim 5 wherein the oxygen or nitrogen substituted amine reacted is a compound of the formula I:

$$R^4\text{—Y—CR}^2\text{—(CH}_2\text{)}_n\text{—CHR}^1\text{—NHR}^3$$ (I)

where
  n is 0, 1, 2, 3;
  Y is O, NH, or $NR^5$;
  $R^1$, $R^2$ are each, independently of one another, H, alkyl, or aryl or $R^1$ and $R^2$, or $R^2$ and $R^3$, or $R^1$ and $R^4$ are, together with adjacent carbon atoms, part of a ring system;
  $R^4$ is alkyl or arylalkyl;
  $R^3$, $R^5$ are, independently of one another, H, alkyl or arylalkyl.

7. The process of claim 6 wherein, in the ester, $R^1$ is $C_1\text{–}C_4$-alkyl and $R^2$ is $C_{1\text{–}C4}$-alkyl.

8. The process of claim 7 wherein in the ester is ethyl methoxyacetate.

9. A process for preparing optically active primary and secondary oxygen or nitrogen substituted amines by
   a) reacting the oxygen or nitrogen substituted amines with an ester of the formula:

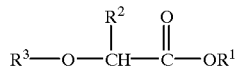

where
$R^1 = C_1-C_{10}$-alkyl,
$R^2 = C_1-C_{10}$-alkyl or H,
$R^3 = $ H, $C_1-C_{10}$-alkyl, or phenyl which is unsubstituted or substituted by $NH_2$, OH, $C^{1-4}$-alkoxy or halogen,
in the presence of a lipase selected from the grout consisting of SP523, SP524, SP525, SP526 and Novozym®435, and
   b) separating of the mixture of optically active oxygen or nitrogen substituted amine and
   optically active acylated oxygen or nitrogen substituted amine to obtain one enantiomer of the oxygen or nitrogen substituted amine.

10. The process of claim 9 wherein the oxygen or nitrogen substituted amine reacted is a compound of the formula I:

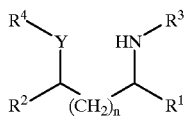

where n is 0, 1, 2, 3;

Y is O, NH, or $NR^5$;

$R^1$, $R^2$ are each, independently of one another, H, alkyl, or aryl or $R^1$ and $R^2$, or $R^2$ and $R^3$, or $R^1$ and $R^4$ are, together with adjacent carbon atoms, part of a ring system;

$R^4$ is alkyl or arylalkyl;

$R^3$, $R^5$ are, independently of one another, H, alkyl or arylalkyl.

11. The process as claimed in claim 10, wherein step b) is followed by another step in which the unwanted enantiomer is racemized and subsequently returned to the racemate resolution process.

12. The process of claim 10 wherein the other enantiomer of the amine from the acylated oxygen or nitrogen substitute is separated by amide cleavage.

13. The process of claim 12 wherein, in the ester, $R^1$ is $C_1-C_4$-alkyl and $R^2$ is $C_1-C_4$-alkyl.

14. The process of claim 13 wherein in the ester is ethyl methoxyacetate.

15. The process of claim 12 wherein the amide cleavage is followed by another step in which the unwanted enantiomer is racemized and subsequently returned to the racemate resolution process.

* * * * *

UNITED STATES PATENT AND TRADEMARK OFFICE
CERTIFICATE OF CORRECTION

PATENT NO. : 6,214,608 B1
DATED : April 10, 2001
INVENTOR(S) : Balkenhohl et al.

It is certified that error appears in the above-identified patent and that said Letters Patent is hereby corrected as shown below:

Column 7, claim 2,
Line 47, "substituded" should be -- substituted --.

Column 8, claim 5,
Line 43, "heteroatom-" should be -- oxygen or nitrogen amine- --.

Column 8, claim 7,
Line 67, "$C_{1-C4}$-alkyl" should be -- $C_1$-$C_4$-alkyl --.

Signed and Sealed this

Sixteenth Day of October, 2001

Attest:

*Attesting Officer*

NICHOLAS P. GODICI
*Acting Director of the United States Patent and Trademark Office*